United States Patent [19]
Matias

[11] Patent Number: 5,874,050
[45] Date of Patent: Feb. 23, 1999

[54] ROOM AIR STERILIZATION DEVICE

[76] Inventor: Carlos J. D. Matias, Av. Paulista 1499, cj 1101/3, Sao Paulo, 01311-928, Brazil

[21] Appl. No.: 675,037

[22] Filed: Jul. 3, 1996

[51] Int. Cl.$^6$ .................................. A61L 9/16; A61L 2/04
[52] U.S. Cl. .............................. 422/120; 422/4; 422/307; 392/465
[58] Field of Search ............................... 422/4, 307, 120; 392/465

[56] References Cited

U.S. PATENT DOCUMENTS

| | | |
|---|---|---|
| 1,333,933 | 3/1920 | Nichols . |
| 1,901,038 | 3/1933 | Marshall . |
| 2,014,455 | 9/1935 | Schwab . |
| 2,564,898 | 8/1951 | Haines . |
| 3,349,224 | 10/1967 | Jaeger . |
| 3,541,304 | 11/1970 | Cohn . |
| 3,654,432 | 4/1972 | Dyre . |
| 3,691,346 | 9/1972 | Dyre et al. . |
| 3,966,407 | 6/1976 | Zuckerberg et al. . |
| 4,233,494 | 11/1980 | Pawlik et al. . |
| 4,536,642 | 8/1985 | Hamster et al. . |
| 4,877,990 | 10/1989 | Fiorenzano ............................... 392/465 |
| 5,326,543 | 7/1994 | Fiorenzano, Jr. . |
| 5,330,723 | 7/1994 | Martin et al. . |
| 5,362,443 | 11/1994 | Tanaka et al. . |
| 5,441,710 | 8/1995 | Marois . |

FOREIGN PATENT DOCUMENTS 1615278 of 0000 Germany .
499074 of 0000 United Kingdom .

Primary Examiner—Mary E. Mosher
Attorney, Agent, or Firm—Malloy & Malloy, P.A.

[57] ABSTRACT

A device for sterilizing a air within a structure, the device having a housing structured to permit air to freely flow therethrough, a base structure coupled with the housing to maintain a bottom of the housing a distance above an underlying surface so as to not obstruct air flowing into the housing, and at least one ceramic heating bundle disposed within the housing. The ceramic heating bundle includes at least two elongate members formed of a ceramic material, disposed in abutting, tight clustered relation with one another, each containing a plurality of narrow, parallel passages structured to permit air to flow therethrough, and at least one heating wire disposed within at least one of the passages of at least one of the elongate members and structured to radiate heat through the ceramic material of the elongate members, thereby heating the air disposed within the passages until the air reaches a sufficient temperature to become sterilized and rise naturally and exit the passages due to convection, thereby creating a vacuum which draws a new supply of ambient air into the passages. The passages are sized and spaced relative to one another within each of the elongate members so as to maximize a ratio of a surface area of ceramic material exposed to the air flowing therethrough, per volume of ceramic material required to define the elongate member, and also to minimize a resistance to heat flow through the ceramic material defining the elongate member and therefore through the ceramic heating bundle.

32 Claims, 4 Drawing Sheets

ROOM AIR STERILIZATION DEVICE

BACKGROUND OF THE INVENTION

1. Field of the Invention

The present invention relates to an improved room air sterilization device directed towards eliminating air-borne germs, bacteria, viruses, and other micro-organisms in indoor environments while causing little, if any, heating of the room temperature where the device is located. In particular, the present invention is seen to include greatly improved and highly efficient air sterilization means comprised of a ceramic material and formed so as to maximize a ratio of surface area of the ceramic material which is exposed to the air per volume of ceramic material utilized in the device and also so as to minimize a resistance to heat flow through the ceramic material. Consequently, air sterilization means having an increased height dimension, without bulkiness, may be utilized so as to permit unsterilized air passing therethrough to have a greater resident air time while simultaneously, to cycle more rapidly throughout the indoor environment where the device is employed.

2. Description of the Related Art

It is commonly known that a wide assortment of harmful and germs, bacteria, viruses, and other micro-organisms exist, some of which remain alive in and are carried by air. This fact presents an especially acute problem to individuals confined to closed or indoor environments where adequate ventilation may not be provided and/or where natural disinfectants such as direct sunlight are not available. Furthermore, closed or indoor environments often retain moisture and dampness which can propagate mold, mildew, fungus, and the like which among other things, can create foul odors. Additionally, the presence of germs, viruses, and bacteria in the air obviously pose substantial health risks including a variety of respiratory problems, harmful illnesses, infections, and contagious diseases. These problems are even more acute for individuals facing particular health risks such as those suffering from a weak or compromised immune system or a sensitive respiratory system, for example.

In the past, those skilled in the art relating to room air sterilization devices have attempted to address these concerns. For example, there are many room dehumidifying devices currently available on the market. Such devices are structured to reduce the amount of moisture in a room so as to reduce the formation of mold, mildew, and fungus. These devices, however, are not oriented towards killing germs, bacteria, viruses, molds, etc. since their primary function is simply to reduce the dampness or moisture content of the air in a room instead of to kill germs, viruses, bacteria, and the like which may be present in the air.

Others have attempted to address this problem by devising room air sterilization devices which are structured to sterilize air by heating it. These known, air sterilization devices have not been entirely satisfactory however. This is because in order to rid the air of germs, bacteria, mold and the like, large quantities of the air must be passed through a device which heats the air to extremely high temperatures. Consequently, known air sterilization devices are believed to significantly raise the temperature of the room where they are located, and consume substantial amounts of energy in the process. Although an increase in the room temperature may be desirable in some situations, such as during the winter or in colder climates, in most instances an increase in a room's temperature is undesirable and renders the air sterilization device impractical for everyday use. To avoid this undesirable result, some have attempted to provide air sterilization devices which heat and sterilize very small quantities of air, but such devices are thought to be either incapable of destroying air-borne germs and bacteria or ineffective in terms of the number of germs and bacteria which are destroyed. It will be appreciated then, that a serious difficulty exists in the art, namely, to provide a device which can heat unsterilized air passing therethrough to the extremely high temperatures required for complete sterilization without significantly raising the temperature of the indoor environment where the device is used.

At least one effort has been made to provide an air sterilization device comprising a large quantity of conductive ceramic material, operably connected with heating elements which produce a quantity of sterilizing heat, and through which air will pass, become heated and thus sterilized. These type of known air sterilization devices are still, however, thought to be inefficient. First, such devices are primarily comprised of a rather large and bulky block or cube of ceramic material mass. Second, bores must then be formed within the mass of ceramic material or it must otherwise be drilled into so as to provide a plurality of air passages therein and through which unsterilized air can pass to become heated and sterilized. It will be appreciated by those skilled in the art that the drilling or boring of holes in ceramic material is almost always done manually, and is a very time-consuming, tedious, and labor-intensive process which constitutes an expensive manufacturing procedure in the production of such air sterilization devices. Furthermore, because these known types of devices generally consist of a single mass of ceramic material it is very difficult to increase or expand the capacity of the devices after manufacture so as to include a greater number of holes or bores in the ceramic or to increase the size of the ceramic material. More significantly, however, it is not possible to drill holes or bores very close to one another in the mass of ceramic material employed by such devices as it is subject to cracking. As such, none of the existing devices provide for substantially thin walls between the air passages, as increasing an overall length of the drilled bores necessarily increases the spacing that must remain therebetween. Specifically, in order to prevent the cracking of the ceramic material, the air passages are bored or drilled a sufficient distance apart from each other so as to ensure thick walls between air passages and prevent the cracking or collapse of the ceramic material. This poses an extremely inefficient design in that a substantial quantity of ceramic material is required to be heated or heated through in order to sterilize a very small quantity of air coming into contact with the surface of the ceramic material. The inefficiency of such devices will be understood when one considers that the unsterilized air passing through the device is cleansed or sterilized only by passing through the heated bores or drilled holes in the mass of ceramic material. Yet, severe limitations exist on the number of bores or drilled holes which can be formed in the block of ceramic material as well as on the diameter of the bores or drilled holes. It is seen, therefore, that in order to achieve an operable air sterilization device, an unnecessary amount of ceramic material mass has had to be utilized, so as to present a sufficient number of heated passages through which unsterilized air may pass, which is a waste of materials. Perhaps worse, an unnecessary amount of energy must also be expended to heat through the entire mass of ceramic material, the majority of which plays no part whatsoever in contacting or sterilizing air, which is again, inefficient. It will also be appreciated from fundamental principals of heat transfer that the greater the distance between the bores or drilled passages within the ceramic block, the more difficult it would be for adjacently disposed passages to share heat provided by a common heating element. Moreover, as heat passes through the ceramic to outer bores within the mass, heat is continually lost when it encounters ceramic material, resulting in greater energy requirements, and resulting in those outer bores not becoming heated to an ideal air sterilizing temperature.

It will be understood that these features of known air sterilization devices which use ceramic material not only reduce efficiency but typically, increase the amount of heat which is dissipated and consequently, raise the temperature of a room where the device is located. One known existing device sought to include ceramic material which utilized bores of a relatively short height, namely, about 4 to 12 centimeters in an effort to avoid causing an increase in the temperature of a room where the device was located. One disadvantage of this type of device is that any one air particle is exposed to the heat within the ceramic material for a much shorter distance than it would in an air passage of greater height, and thus, air flow through the short air passages must be slower if the same degree of sterilization is to be provided. Another problem with this type of device is that even though the air passages very near or directly in contact with a heating wire become sufficiently hot to sterilize the air, the air passages at or near the outer peripheral walls of the ceramic material mass cannot approximate the same temperature as heat is lost as it passes through the large masses of ceramic material between adjacent air passages, and heat is lost to the air around the exterior of the ceramic material mass. Consequently, existing devices are not able to uniformly heat all of the air passages within the ceramic material and the air exiting these devices is inconsistently sterilized.

Accordingly, there still remains a significant need in the art for an improved room air sterilization device which can eliminate air-borne germs, bacteria, viruses, and other microorganisms without raising the temperature of the room where it is located. In particular, there is a need for a room air sterilization device which utilizes greatly improved and highly efficient air sterilization means in the form of ceramic material formed to minimize the amount of ceramic material which is not exposed to the air and which may resist heat flow, to promote the sharing of heat between air passages, to allow for air passages having a taller height dimension, thereby resulting in a greater resident air time, faster air cycle time and greater disbursement into larger rooms than would have been possible utilizing known devices. There is also a need for an air sterilization device which permits the air sterilization capacity of the device to be expanded by allowing facilitated attachment of additional air sterilization means, after or before the device has been completely manufactured and assembled. The present invention is specifically designed to address these needs which remain in the art.

SUMMARY OF THE INVENTION

The present invention relates to an improved air sterilization device and is structured to eliminate germs, bacteria, viruses, and other micro-organisms found in the air in indoor environments, without substantially raising the temperature of the room where the device is located. The air sterilization device of the present invention comprises improved air sterilization means in the form of at least one elongate member formed of a ceramic material, having a first end and a second end, and plurality of narrow, substantially parallel passages extending therebetween for permitting air to flow therethrough. The plurality of narrow, substantially parallel passages are sized and spaced relative to one another within the elongate member so as to maximize a ratio of the ceramic material surface area exposed to the air and from which heat will radiate, per volume of ceramic material utilized in the device and to minimize a resistance to heat flow through the ceramic material. The air sterilization means additionally comprise at least one heating wire disposed and extending within at least one of the narrow, substantially parallel passages. The heating wire is structured and disposed to radiate substantial quantities of heat through the ceramic material of the elongate member so as to heat the parallel passages, and thereby, to heat the air disposed within the narrow, substantially parallel passages of the elongate member until the air reaches a sufficient temperature to become sterilized and to rise naturally, exiting the elongate member, creating a vacuum therein and drawing a new supply of air into the narrow, substantially parallel passages of the elongate member.

In another embodiment of the present invention, the air sterilization means comprise at least one ceramic heating bundle having a plurality of the elongate members disposed in an abutting, substantially tight clustered relation with one another. Most preferably, the ceramic heating bundle includes seven elongate members, each disposed in substantially parallel relation with another.

In the preferred embodiment, the air sterilization device of the present invention includes a housing, in which the air sterilization means are disposed. The housing preferably includes a top, a bottom, and a surrounding sidewall defining a generally hollow interior portion. The top and bottom of the housing are preferably structured to permit air to flow freely therebetween and through the housing, and as such, the invention may additionally include a base structure operably coupled to the housing and structured to maintain the bottom of the housing above an underlying surface so that the air flowing through the bottom of the housing is not obstructed. Alternatively, the top and at least a lower portion of the surrounding sidewall of the housing may be structured to permit air to flow freely therebetween and through the housing, and as such, the invention may additionally include means for suspending the air sterilization means within the housing a spaced apart distance above the bottom of housing, which may itself then be placed directly on an underlying surface.

A primary object of the present invention is to eliminate air-borne germs, bacteria, viruses and other microorganisms found in a closed or indoor environment by cycling the air within that environment through a device which heats the air passing therethrough to a sufficiently elevated temperature so as to sterilize it.

Another primary object of the present invention is to provide such an air sterilization device which does not substantially raise the temperature of the enclosed area in which the device is employed.

It is also a primary object of the present invention is to provide greatly improved and highly efficient air sterilization means comprising ceramic material which is formed, structured and disposed to maximize a ratio of the ceramic material surface area exposed to the air and through which heat will radiate, per volume of ceramic material utilized in the device, and to minimize a resistance to heat flow through the ceramic material.

An advantage of the improved air sterilization means of the present invention is that it provides for narrow, substantially parallel passages within a ceramic material, which passages may have a larger height dimension to thereby cause the air passing therethrough to be subjected to a longer travel path along which sterilization occurs and to travel more quickly through the device.

Another advantage of the present invention is that the improved room air sterilization means promote the sharing of heat between adjacently disposed, narrow, substantially parallel passages.

A further advantage of the present invention is that the improved room air sterilization means are able to achieve a higher sterilization capacity due to the higher air speed that is achieved through the longer passages and the increased sterilized air disbursement attained by the faster air flow.

Yet another object of the present invention is to provide an improved room air sterilization device which permits the capacity of the device to sterilize a volume of air to be expanded by allowing for the facilitated installation of additional air sterilization means, either before or long after the device has been manufactured and assembled.

These and other objects, features and advantages of the present invention will become more readily apparent from the attached drawings and the detailed description of the preferred embodiments, which follows.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Shown throughout the Figures, the present invention is orientated towards an improved air sterilization device, generally indicated as 10. The improved air sterilization device 10 is directed towards the elimination of germs, bacteria, viruses, and other micro-organisms found in the air in closed or indoor environments, without raising the temperature of the enclosed area where the device is located.

Figure 3:
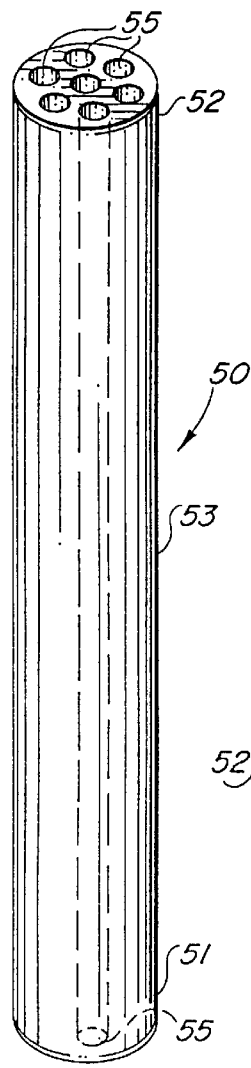
FIG. 3 is a front perspective view of one embodiment of the air sterilization means according to the present invention in the form of one elongate member.

The air sterilization device 10 of the present invention is first seen to comprise air sterilization means 40 for sterilizing the air found within a closed environment. The air sterilization means 40 of the present invention include means for heating air, either directly or indirectly, in order to achieve sterilization and in order to cause the air to circulate, by convection, through the device 10 and thereby, sterilize the air found within the environment where the device 10 is located. In one embodiment, the air sterilization means 40 may comprise a single elongate member 50, illustrated in FIG. 3, which is preferably formed of a ceramic material. Still referring to FIG. 3, the elongate member 50 is seen to include a first end 51 and a second end 52. While those skilled in the art will appreciate that the elongate member 50 may be configured in a wide variety of shapes, such as a generally square or rectangular configuration, in a more preferred embodiment, the elongate member 50 will have a generally cylindrical appearance as shown in the drawings. As explained below, in a most preferred embodiment, the elongate member will have a length of about five inches (5") between ends 51, 52 and will have an outer diameter of about one-half inch (½").

Additionally, the elongate member 50 will include a plurality of narrow, substantially parallel passages 55 extending from the first end 51 to the second end 52 of the elongate member 50. These passages 55 permit air 70 to freely flow into the elongate member 50 at one end, such as first end 51, through the length of elongate member 50, and to exit the elongate member at another end, such as second end 52. moreover, the passages 55 provide an effective confined space within which the air 70 can be more effectively heated. A particularly novel feature of the present invention is the placement and sizing of the narrow, substantially parallel passages 55 within the elongate member 50. Before this feature is described, however, it may be helpful to discuss the means for heating the air employed with the air sterilization means 40.

More specifically, the air sterilization means 40 of the present invention additionally comprise means for heating air, either directly or indirectly, which heating means are first seen to comprise at least one heating wire 60. The heating wire 60 is operably connected to additional heating means and is structured and disposed to radiate heat through the ceramic material of the elongate member 50 and into the passages 55, thereby, to heating the air disposed within the narrow, substantially parallel passages 55 until the air reaches a sufficient temperature to become sterilized and to rise naturally and to exit the elongate member 50, creating a vacuum therein and drawing a new supply of unsterilized air into the narrow, substantially parallel passages 55 of the elongate member 50. The heating wire 60 is disposed inside at least one of the narrow, substantially parallel passages 55 of the elongate member 50, although in the preferred embodiment, the heating wire 60 will be threaded through and will extend through a plurality, if not all of the narrow, substantially parallel passages 55 of elongate member 50. If desired, a plurality of separate but operably connected heating wires 60 may also be used. In a most preferred embodiment, the heating wire 60 is formed of a nickel chromium (NiCr), resistive material, having a thin outer diameter of about $2/10$ millimeters, although those skilled in the art will appreciate that the heating wire 60 may be formed of another suitable material without departing from the scope of the present invention. As indicated, the heating wire 60 is operably connected to additional heating means which are structured and disposed to heat the heating wire 60 to an elevated temperature At a minimum, a temperature, such as 170 degrees Celsius, which is sufficient to sterilize air, as well as to cause the air to rise naturally by convection which be attained. The additional heating means may therefore include a power source structured and disposed to supply electrical current to the heating wire 60. For example, the power source may comprise AC/DC current, or if desired, could be a battery or even, a solar powered source of electrical energy. If desired, two separate sets of heating wires 60 may be utilized in the device 10, each set of heating wires being structured and disposed to be independently activated and to thereby, permit a user to selectively adjust a level of air sterilization required for a particular indoor environment.

Figure 4:
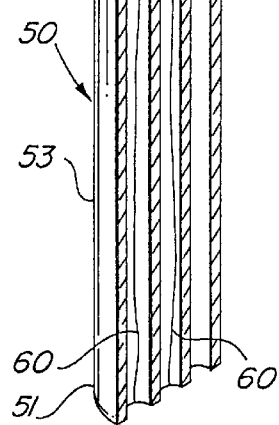
FIG. 4 is a cross sectional view of the elongate member illustrated in FIG. 3 which more clearly illustrates the narrow substantially parallel passages extending therethrough as well as a heating wire extending therethrough.

Referring back now to FIG. 3, and to FIG. 4, a particularly novel feature of the present invention will now be described. Before that can be done, however, it should be readily understood that the air to be treated within the indoor environment will primarily, only be heated and sterilized when it passes through the heated ceramic material forming the elongate member 50, in that although heat may also transfer from the outer peripheral regions of the ceramic material forming elongate member 50, it dissipates into the air surrounding the elongate member 50 and thereby is not effective to sterilize the air surrounding the member 50. It would therefore be advantageous to maximize the exposure of ceramic material, through which the heat will radiate, to unsterilized air passing through the passages 55 defined by the ceramic material, while both limiting the amount of ceramic material exposed to the air surrounding the ceramic material and avoiding a bulky, cumbersome mass of ceramic material. The present invention accomplishes this difficult objective in that the plurality of narrow, substantially parallel passages 55 extending within elongate member 50 are sized and spaced relative to one another so as to maximize a ratio of the ceramic material surface area exposed to the air, and from which the heat will radiate, per volume of ceramic material utilized in the device, and further, to minimize a resistance to heat flow through the ceramic material by minimizing the thickness of ceramic material through which the heat must flow. In more simple terms, the placement and sizing of the narrow, substantially parallel passages 55 within the elongate member 50 will now be discussed. First, the inventor herein has discovered that the elongate member 50 can be readily formed by an extrusion process, not previously contemplated, in order to define the narrow, substantially parallel passages 55 extending therethrough. The extrusion process essentially permits the narrow, substantially parallel passages 55 to be formed extremely close to one another within the elongate member 50 and thereby, to minimize an overall amount of ceramic material utilized to form elongate member 50 while at the same time, maximizing the surface area of the ceramic material from which the heat will be radiated and which contacts unsterilized air passing through the passages 55 defined by the ceramic material of elongate member 50. As shown in FIG. 4, in a preferred embodiment each of the narrow passages 55 within the elongate member 50 are formed to be cylindrical and substantially parallel to one another, and the thickness of the ceramic material separating the passages 55 is substantially minimized, thereby providing minimal resistance and/or dissipation of heat flow as it passes from one passage 55 to another. As also illustrated in FIG. 4, in the most preferred embodiment, seven passages 55 are formed within elongate member 50, with ideally, a first passage disposed at and aligned with a central longitudinal axis of elongate member 50 and six passages disposed concentrically in a circular pattern thereabout. It will be appreciated, however, that a smaller number of passages 55 or a larger number of passages 55 may be formed in elongate member 50 without departing from the scope of the present invention. Additionally, in the preferred embodiment, the outer diameter of any one passage 55 extending within the elongate member 50 is between generally about 2 millimeters and 4 millimeters, and ideally, about 3 millimeters. Also in the preferred embodiment, the maximum distance of ceramic material forming the elongate member 50 between any two, adjacently disposed, narrow passages 55 is generally about two millimeters, and ideally, generally about one and one-half (1.5) millimeters. With respect to the thickness of ceramic material between the outer exposed wall 53 defining the elongate member 50 and any one of the narrow, substantially parallel passages 55, the adjacent outer exposed wall 53 is at least about one and one-half (1.5) millimeters, but preferably will be a bit thicker, such as between generally about 2 and 10 millimeters, so as to safeguard the thin ceramic material disposed about and forming narrow passages 55. This arrangement or placement and sizing of the plurality of narrow passages 55 within elongate member 50, has been determined to reduce the resistance to heat flow through the ceramic material defining the elongate member 50 so as to substantially promote sharing of heat between passages 55 and thereby, concentrate heat within the longitudinal core of elongate member 50. Thus, the efficiency of the air sterilization device is thought to have substantially improved.

Additionally, the extrusion process allows the formation of an elongate member 50 which is taller, that is, which has a larger height dimension between first and second ends 51, 52 than may have been commonly used in other devices utilizing blocks of ceramic material. As has been described, preferably, the height dimension of elongate member 50 between first end 51 and second end 52 is at least five (5") inches. The ability to form both taller and narrow, substantially parallel passages 55 within ceramic material which are very closely disposed to each other is primarily due to the fact that these passages 55 are not drilled or bored into the ceramic material, as was done in the past, but are formed instead during the extrusion of the elongate member 50, which yields unexpected results in terms of the efficiency of the air sterilization means 40 comprising one or more of elongate members 50. More specifically, the prior art methods of forming passages in ceramic material by drilling or boring holes into the ceramic material resulted in passages having much larger outer diameters as well as greater wall thickness between each passage. This is due to the fact that ceramic material is brittle and can easily crack or become fragmented when being drilled or bored into. The taller size of the passages 55 within the elongate member 50 translates to the following: any one air particle traveling therethrough is exposed to the heat radiated through the ceramic material for a longer distance, that is, a greater air sterilization distance. Also, the taller size of the passages 55 permit faster air cycle time; air flow through a taller passage 55 may be more rapid while still permitting proper sterilization to occur, thereby permitting air to circulate through the device at a faster rate and therefore the overall circulation of sterilized air throughout a room or other enclosed area is improved significantly, without a substantial increase in the temperature of the room or other enclosed area.

Figure 2:
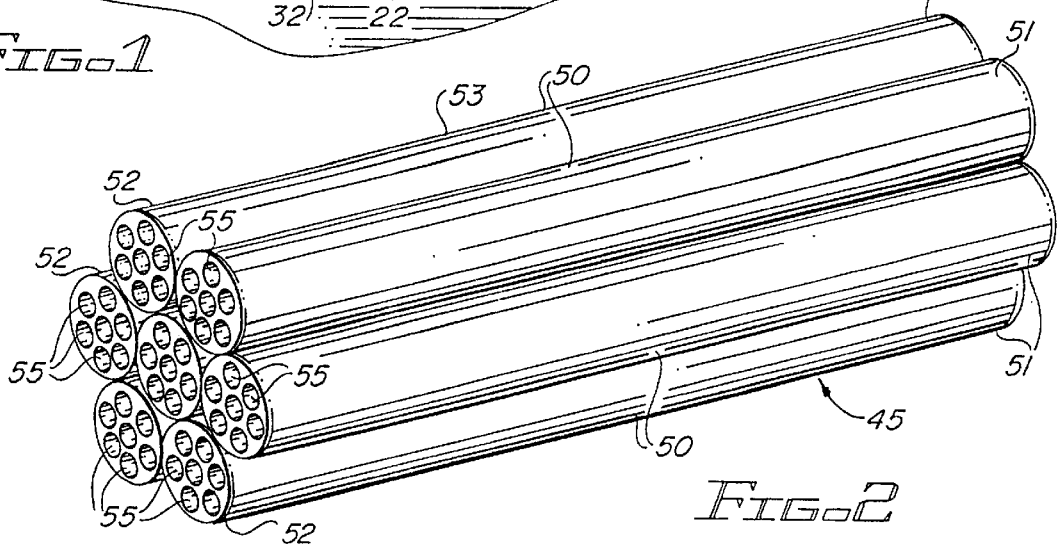
FIG. 2 is a perspective view showing a preferred embodiment of the air sterilization means according to the present invention in the form of a ceramic heating bundle.
Figure 6:
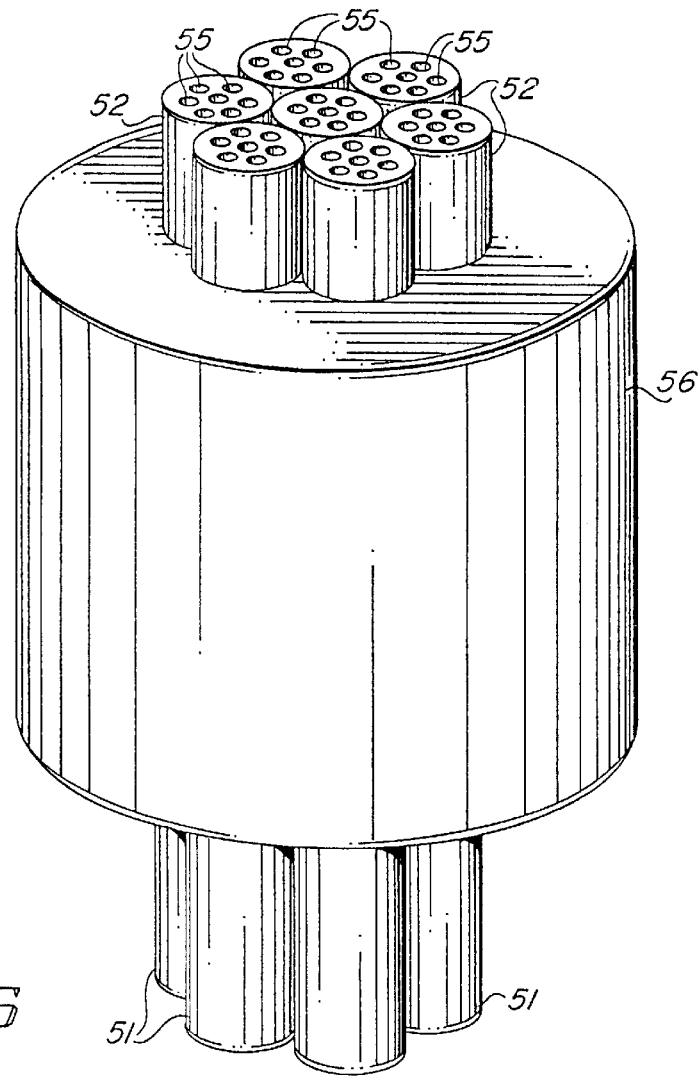
FIG. 6 is a perspective view of an alternative embodiment of the ceramic heating bundle including an insulative material shell disposed in surrounding relation thereto.

Referring now to FIG. 2, a more preferred embodiment of the air sterilization means 40 is illustrated and is seen to comprise at least one ceramic heating bundle 45 formed by a plurality of the elongate members 50. Preferably, each elongate member 50 forming the ceramic heating bundle 45 is disposed in an abutting, substantially tight, clustered relation with each other elongate member 50. Most preferably, each elongate member 50 is also disposed within the ceramic heating bundle 45 in generally parallel relation to each other elongate member 50 to maximize the efficiency of air sterilization means, although variations from parallel relation can occur. Ideally, the ceramic heating bundle 45 comprises seven elongate members 50, each of a substantially equal height dimension and with first ends 51 or second ends 52 aligned with one another. In this more preferred embodiment of air sterilization means, at least one heating wire 60 should be disposed within each elongate member 50 of the ceramic heating bundle 45. Here again however, more than one heating wire 60 may be utilized per elongate member 50 of the bundle 45, although it may be desirable in some situations to have an elongate member 50 which does not contain any heating wires 60. Moreover, in an alternative embodiment illustrated in FIG. 6, an insulative material shell 56 may be disposed in surrounding relation about the ceramic heating bundle 45 so as to minimize exterior heat loss therefrom.

Figure 1:
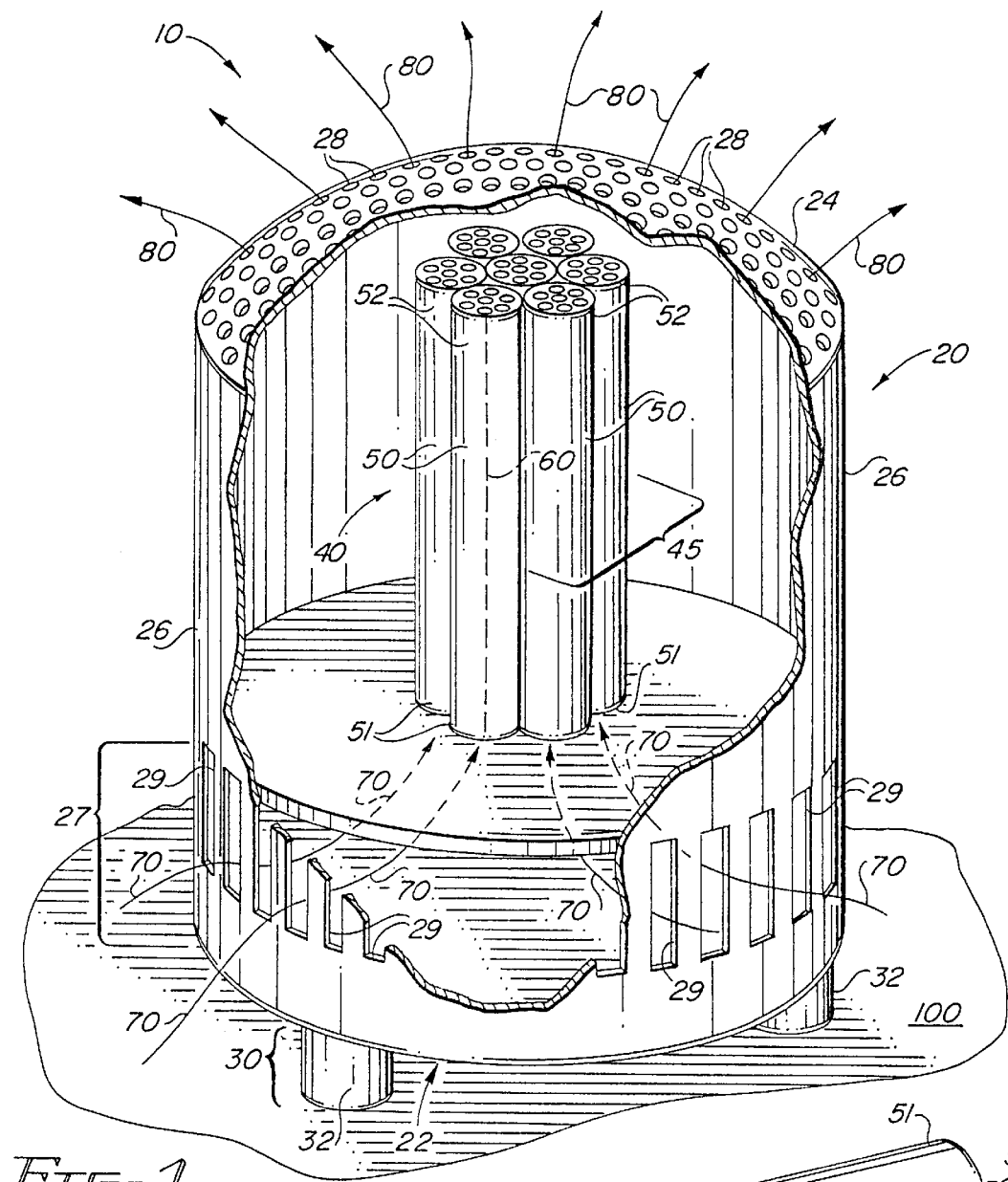
FIG. 1 is a front perspective front view of a preferred embodiment for the improved air sterilization device of the present invention.
Figure 7:
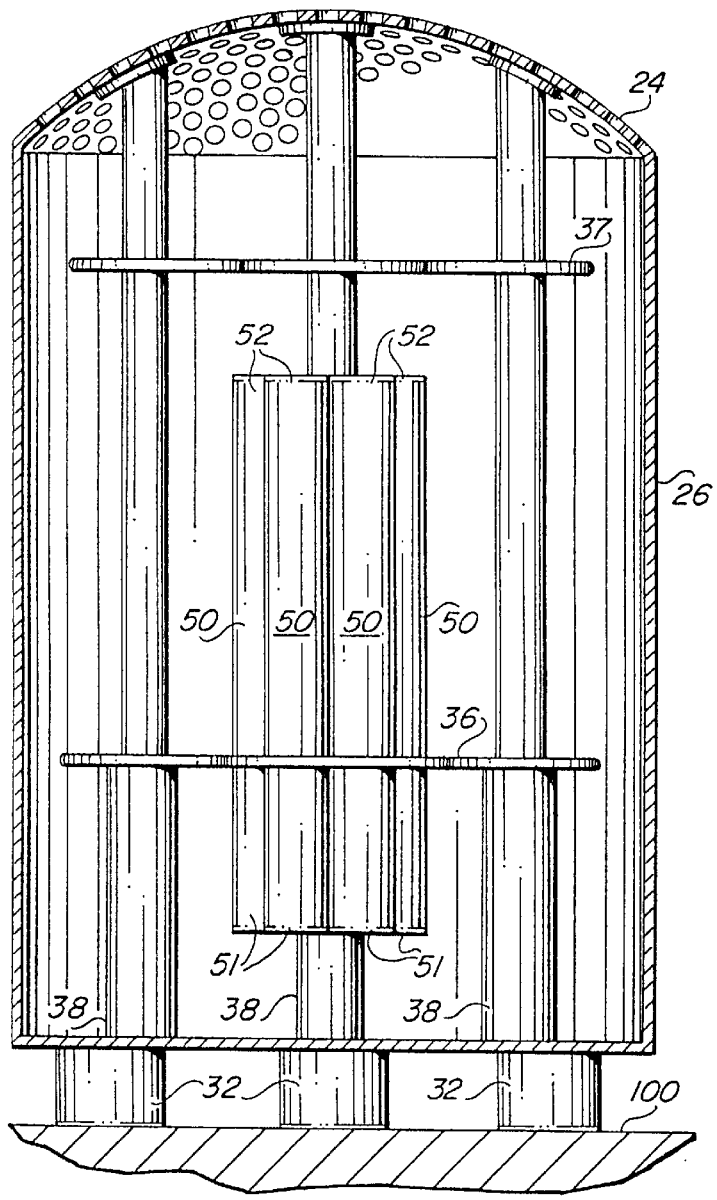
FIG. 7 is a side, cross-sectional view of an alternative embodiment of the present invention including a diffuser panel disposed above the ceramic heating bundle.
Figure 5:
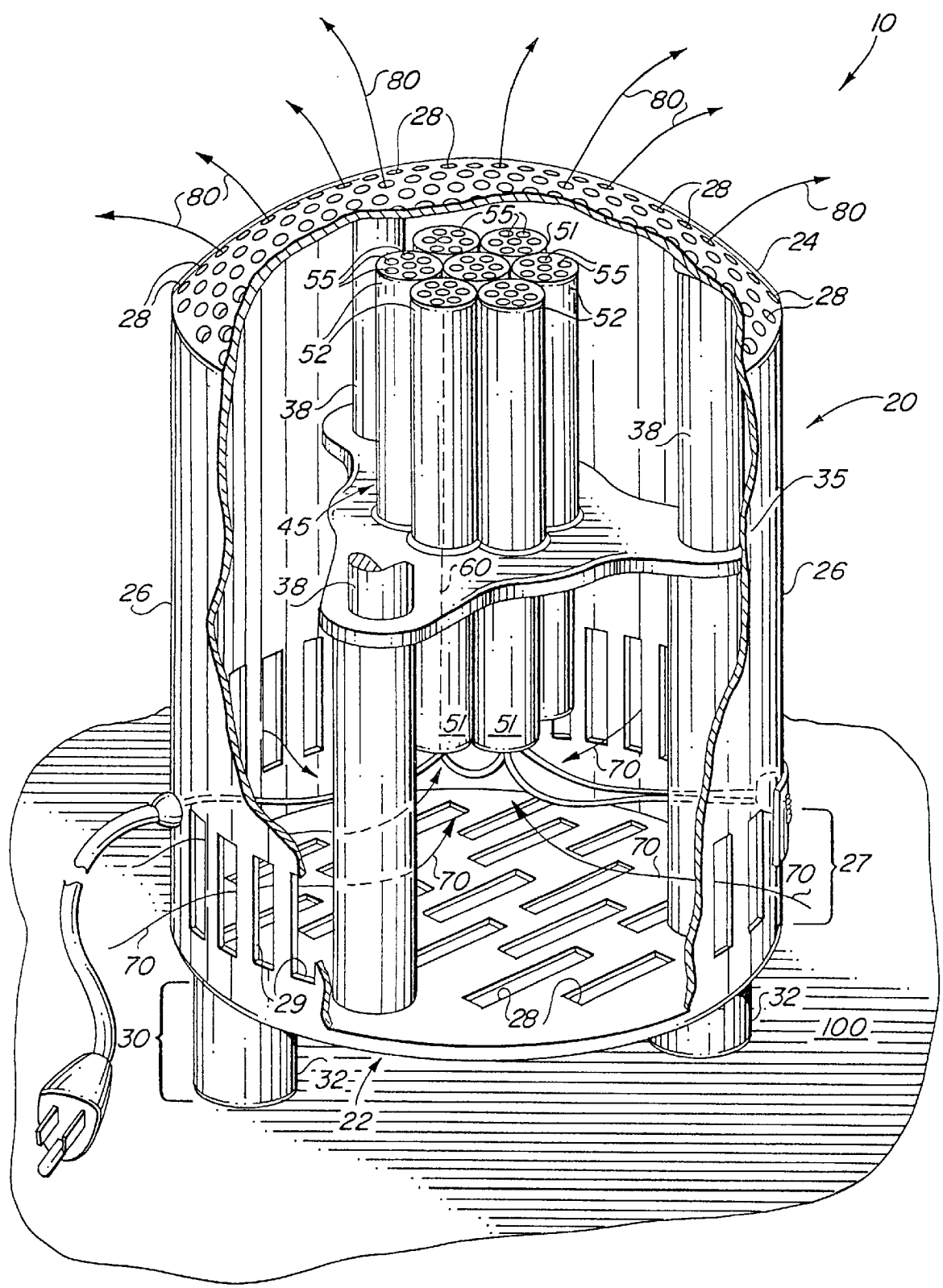
FIG. 5 is a front perspective front view of a more preferred embodiment for the improved air sterilization device of the present invention.
Figure 8:
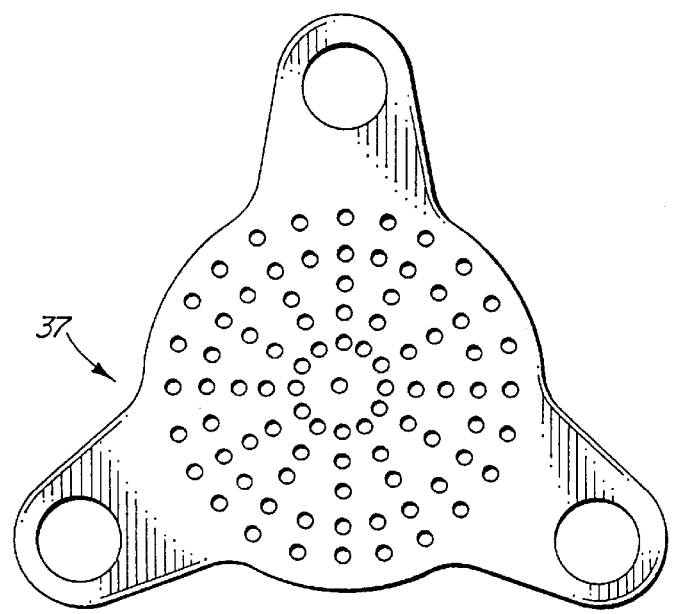
FIG. 8 is a top perspective view of the diffuser panel of FIG. 7.

Referring now to FIG. 1, in the preferred embodiment, the air sterilization device 10 of the present invention additionally comprises a housing 20, in which the air sterilization means 40 are disposed. While it is contemplated, that the air sterilization means 40 of the present invention may be disposed in a very small, enclosed environment, for example in an air conditioning duct where a housing would not be necessary, in most instances the air sterilization device 10 will additionally comprise a housing 20. The housing 20 is seen to include a bottom 22, a surrounding sidewall 26 defining a generally hollow interior portion therein, and preferably, a top 24. It will be appreciated by those skilled in the art that the surrounding sidewall 26 of the housing 20 may be formed in a wide variety of shapes. The housing can, for example, be structured in a generally box-like configuration. In the preferred embodiment, however, the sidewall 26 of the housing 20 is structured in a generally cylindrical manner, as shown in FIG. 1. The housing 20 may be constructed of a wide variety of durable rigid materials such as aluminum, steel, another metal, plastic or a like material which is not subject to warping, melting, or otherwise being damaged by heat. The housing 20 is structured to permit air to flow freely therethrough. In one embodiment, this may be accomplished by both the bottom 22 and the top 24 of the housing being formed to include a plurality of apertures 28 therein. In another embodiment, both the top 24 of the housing and a lower portion 27 of the surrounding sidewall 26 of the housing 20 may be formed to have a plurality of apertures or slits such as 29 therein. In the preferred embodiment however, illustrated in FIG. 1, both the bottom 22 and lower portion 27 of the surrounding sidewall 26 of the housing 20, as well as top 24 are formed to have a plurality of apertures 28 therein, so as to maximize air flow through housing 20. It will be appreciated from the foregoing that unsterilized air is permitted to enter through apertures 28 in the bottom 22 and/or lower portion 27 of surrounding sidewall 26 of the housing 26 as shown in FIG. 1, and that air will be permitted to exit from the top 24 of the housing 20 in a substantially sterilized condition. In a more preferred embodiment, the top 24 of the housing 20 may be formed to be convex so at to provide a dome shape to the top of the device 10, which is thought to aid the increased efficiency of the device 10 in sterilizing air. If desired, the top 24 of the housing 20 may be configured with smaller diameter apertures and/or a fewer number of them so as to create additional turbulence in the exiting airflow, thereby allowing it to substantially cool before exiting the housing 20. Moreover, in yet another embodiment, as illustrated in FIGS. 7 and 8, an additional diffuser panel 37 may be disposed between the top 24 of the housing 20 and the elongate members 50 so as to further diffuse and cool the air exiting the housing 20.

As illustrated in FIG. 1, the air sterilization device 10 of the present invention may additionally include a base structure 30. In the preferred embodiment, the base structure 30 is operably coupled to the housing 20 and is structured to maintain the bottom 22 of housing above an underlying surface 100 so that the air flowing through the bottom of the housing is not obstructed. The underlying surface 100 may be a floor, desk, table, counter-top, or any generally flat surface upon which the air sterilization device 10 may be placed. It will be appreciated by those skilled in the art that the base structure 30 may be configured in a wide variety of shapes capable of maintaining the bottom 22 of the housing 20 a distance above an underlying surface 100 so that the air flowing through the bottom 22 of the housing 20 is not obstructed. In the preferred embodiment, the base structure 30 will include a plurality of leg members 32 disposed on the bottom surface 22 of the housing 20 as shown in FIG. 1. The leg members 32 may include any of a wide variety of shapes, although in the preferred embodiment, three cylindrical leg members 32 will be utilized and disposed in a tripod like manner on the bottom 22 of the housing 20.

Still referring to FIG. 1, the air sterilization device 10 of the present invention may also comprise means for suspending the air sterilization means 40 within the housing 20. The suspending means 36 may comprise means for suspending one or more elongate members 50 or one or more ceramic heating bundles 45, in most preferably, a generally vertical orientation within the housing 22 and in spaced apart relation from surrounding side wall 26. In the preferred embodiment, the suspending means 35 comprise bundle disposing means in the form of a rigid collar member 36 disposed at least substantially about the circumference of a ceramic heating bundle 45 and a plurality of column supports 38 operably coupled to and extending within the housing 22. Ideally, each one of the column supports 38 is operably coupled to bottom 22 of the housing as well as to the top 24 thereof, with each column support 38 also being operably coupled to the rigid collar member 36 which extends about the ceramic heating bundle 45. It will be appreciated that in the embodiment of the device 10, where a base structure 30 is employed, the suspending means 35 may not be needed as the air sterilization means 40 may be disposed within housing 20 in contact with the upper wall of bottom 22. In the preferred embodiment, and in the embodiment where no base structure 30 is employed, meaning that the bottom 22 of the housing 20 may be in direct contact with a support surface 100, the suspending means 35 are utilized so as to permit the unsterilized air 70 flowing into the housing through surrounding sidewall 26 to freely flow into first end 51 of one or more elongate members 50.

Finally, the air sterilization capacity of the device 10 according to the present invention may be expanded. Specifically, additional air sterilization means 40, in the form of one or more elongate members 50 may be easily added to the ceramic heating bundle 45, even after the device 10 has been manufactured and assembled. It will be appreciated that this is because the bundle disposing means comprising a rigid collar member may be adjusted about a circumference of the ceramic heating bundle 45.

The use of the preferred air sterilization device 10 will now be described. Referring to FIG. 1, it is seen that unsterilized air 70 enters the housing 20 at a lower end thereof and travels into first ends 51 of the elongate members 50 of the ceramic heating bundle 45. The elongate members 50 of the ceramic heating bundle 45 are substantially heated by the heating wires 60, which are operably connected to both means for heating and a power source structured and disposed to supply an electrical current thereto and to cause a rise in temperature to generally about 170 degrees celsius. It is also seen that the heating wires 60 are disposed within the narrow, substantially parallel passages 55 of the elongate members 50 so as to radiate heat through the ceramic material forming the elongate members 50 and the ceramic heating bundle 45, and heat the air disposed within each of the narrow, substantially parallel passages 55. As the air in each of the narrow, substantially parallel passages 55 is exposed to the heat radiating through the ceramic material forming the passages 55, it becomes heated to a temperature sufficient to sterilize it and kill air borne germs, bacteria, mold, and other micro-organisms and further, begins to rise naturally due to convection until it exists the second end 52 of the narrow, substantially parallel passages 52. In the preferred embodiment wherein the top 24 of the housing has a convex or dome shaped configuration, the sterilized air 80 has an opportunity to begin cooling as it exits the second ends 52 of the elongate members 50 of the ceramic heating bundle 45 until it reaches the top 24 of the housing 24. Additionally, if the top 24 of housing 20 has been provided with apertures 28 having smaller outer diameters and/or a smaller number of apertures, some of the sterilized air 80 will be forced to cycle within housing 20, either between the top 24 of the housing and second ends 52 of the elongate members or the surrounding sidewall 26 of the housing and the ceramic heating bundle 45 and it will therefore be appreciated that the positioning of the ceramic heating bundle 45 in this preferred embodiment forms a cooling chamber within the housing 20 and about the bundle 45. If desired, the housing 20 may additionally comprise means for signaling when the air sterilization means 40 have been activated, which preferably, include an exteriorly disposed light source structured to be illuminated upon activation of the air sterilization means 40.

Since many modifications, variations and changes in detail can be made to the described preferred embodiments of the invention, it is intended that all matters in the foregoing description and shown in the accompanying drawings be interpreted as illustrative and not in limiting sense. Thus, the scope of the invention should be determined by the appended claims and their legal equivalents.

What is claimed is:

1. A device for sterilizing a quantity of air, said device comprising:

air sterilization means comprising:
    i. at least one elongate member formed of a ceramic material and including a first end and a second end;
    ii. each elongate member including a plurality of narrow, substantially parallel passages extending from said first end to said second end so as to permit air to flow therethrough;
    iii. at least one heating wire disposed and extending within at least one of said narrow, substantially parallel passages of said elongate member;
    iv. said plurality of narrow, substantially parallel passages being sized and spaced relative to one another within said elongate member so as to maximize a ratio of a surface area of ceramic material exposed to the air flowing therethrough per volume of ceramic material required to define said elongate member and also to minimize a resistance to heat flow through said ceramic material defining said elongate member between said narrow, substantially parallel passages;
    v. said heating wire being structured and disposed to radiate heat through said ceramic material of said elongate member and thereby heat the air disposed within said narrow, substantially parallel passages of said elongate member to a temperature sufficient to sterilize the air and to cause the air to rise naturally due to convection and exit said narrow, substantially parallel passages of said elongate member, creating a vacuum therein which draws a new supply of ambient air into said narrow, substantially parallel passages of said elongate member; and
    vii. means operably connected to said heating wire for heating said heating wire.

2. An air sterilization device as recited in claim 1 wherein said elongate member is formed by an extrusion process capable of defining said narrow, substantially parallel passages therein.

3. A device for sterilizing a quantity of air, said device comprising:

air sterilization means comprising:
    i. at least one ceramic heating bundle having at least two elongate members disposed in abutting, substantially tight, clustered relation with one another;
    ii. each of said elongate members being formed of a ceramic material and including a first end and a second end;
    iii. each of said elongate members including a plurality of narrow, substantially parallel passages extending from said first end to said second end so as to permit air to flow therethrough;
    iv. at least one heating wire disposed and extending within at least one of said narrow, substantially parallel passages of at least one of said elongate members of said ceramic heating bundle;
    v. said plurality of narrow, substantially parallel passages being sized and spaced relative to one another within each of said elongate members so as to maximize a ratio of a surface area of ceramic material exposed to the air flowing therethrough per volume of ceramic material required to define said elongate member and also to minimize a resistance to heat flow through said ceramic material defining said elongate member between said narrow, substantially parallel passages and therefore through said ceramic heating bundle;
    vi. said heating wire being structured and disposed to radiate heat through said ceramic material of said elongate members forming said ceramic heating bundle and thereby heat the air disposed within said narrow, substantially parallel passages of said elongate members to a temperature sufficient to sterilize the air and to cause the air to rise naturally due to convection and exit said narrow, substantially parallel passages of said elongate members, creating a vacuum therein which draws a new supply of ambient air into said narrow, substantially parallel passages of said elongate members; and
    vii. means operably coupled to said at least one heating wire for heating said heating wire.

4. An air sterilization device as recited in claim 3 further comprising means for retaining said elongate members within said ceramic heating bundle and wherein said ceramic heating bundle is placed within an airflow conduit.

5. An air sterilization device as recited in claim 3 wherein each of said elongate members are formed by an extrusion process capable of defining said narrow, substantially parallel passages.

6. A device for sterilizing a quantity of air, said device comprising:
a) a housing including a bottom, a top, and a surrounding sidewall defining a generally hollow interior therein, said surrounding sidewall including a lower portion generally adjacent said bottom, said lower portion and said top being structured to permit the air to freely flow therebetween and through said housing;
b) air sterilization means comprising:
  i. at least one elongate member disposed within said housing;
  ii. said elongate member being formed of a ceramic material and including a first end and a second end;
  iii. said elongate member including a plurality of narrow, substantially parallel passages extending from said first end to said second end so as to permit air to flow therethrough;
  iv. at least one heating wire disposed and extending within at least one of said narrow, substantially parallel passages of said elongate member;
  v. said plurality of narrow, substantially parallel passages being sized and spaced relative to one another within said elongate member so as to maximize a ratio of a surface area of ceramic material exposed to the air flowing therethrough per volume of ceramic material required to define said elongate member and also to minimize a resistance to heat flow through said ceramic material defining said elongate member between said narrow, substantially parallel passages;
  vi. said heating wire being structured and disposed to radiate heat through said ceramic material of said elongate member and thereby heat the air disposed within said narrow, substantially parallel passages of said elongate member until the air reaches a sufficient temperature to become sterilized and rises naturally due to convection and exits said narrow, substantially parallel passages of said elongate member, creating a vacuum therein which draws a new supply of ambient air into said narrow, substantially parallel passages of said elongate member;
  vii. means operably coupled to said at least one heating wire for heating said heating wire; and
c) means for suspending said elongate member within said housing in a substantially vertical orientation and a spaced apart distance above said bottom of said housing.

7. A device for sterilizing a quantity of air within a structure, said device comprising:
a) a housing including a bottom, a top, and a surrounding sidewall defining a generally hollow interior therein, said bottom and top structured to permit the air to freely flow therebetween and through said housing;
b) a base structure operably coupled to said housing and configured to maintain said bottom of said housing a distance above an underlying surface so as to not obstruct the air flowing through said bottom of said housing; and
c) air sterilization means comprising:
  i. at least one ceramic heating bundle disposed within said housing, said ceramic heating bundle including at least two elongate members disposed in abutting, substantially tight clustered relation with one another;
  ii. each of said elongate members being formed of a ceramic material and including a first end and a second end;
  iii. each of said elongate members including a plurality of narrow, substantially parallel passages extending from said first end to said second end so as to permit air to flow therethrough;
  iv. at least one heating wire disposed and extending within at least one of said narrow, substantially parallel passages of at least one of said elongate members of said ceramic heating bundle;
  v. said plurality of narrow, substantially parallel passages being sized and spaced relative to one another within each of said elongate members so as to maximize a ratio of a surface area of ceramic material exposed to the air flowing therethrough per volume of ceramic material required to define said elongate member and also to minimize a resistance to heat flow through said ceramic material defining said elongate member between said narrow, substantially parallel passages and therefore through said ceramic heating bundle;
  vi. said heating wire being structured and disposed to radiate heat through said ceramic material of said elongate members forming said ceramic heating bundle and thereby heat the air disposed within said narrow, substantially parallel passages of said elongate members until the air reaches a sufficient temperature to become sterilized and rise naturally due to convection and exit said narrow, substantially parallel passages of said elongate members, creating a vacuum therein which draws a new supply of ambient air into said narrow, substantially parallel passages of said elongate members; and
  vii. means operably coupled to said at least one heating wire for heating said heating wire.

8. An air sterilization device as recited in claim 7 wherein said bottom and said top of said housing include a plurality of apertures formed therein.

9. An air sterilization device as recited in claim 7 wherein said surrounding sidewall includes a lower portion generally adjacent said bottom, said lower portion also including a plurality of apertures formed therein for permitting the air to freely flow into said lower portion of said surrounding sidewall and through said top of said housing.

10. An air sterilization device as recited in claim 7 further comprising means for disposing said bundle in a generally vertical orientation within said housing.

11. An air sterilization device as recited in claim 10 wherein said bundle disposing means also disposes said bundle a spaced apart distance above said bottom of said housing.

12. An air sterilization device as recited in claim 11 wherein said bundle disposing means comprise:
a) a rigid collar member disposed at least substantially about a circumference of said bundle;
b) a plurality of column supports operably coupled to and extending within said housing from said bottom of said housing to said top of said housing, each of said column supports being operably coupled to said collar member.

13. An air sterilization device as recited in claim 12 wherein said collar member includes means for adjusting said collar between a first position wherein said collar is disposed in a close surrounding relation about said bundle and a second position wherein said collar is disposed loosely about said bundle.

14. An air sterilization device as recited in claim 12 wherein said bundle disposing means further dispose said bundle a spaced apart distance from said surrounding sidewall of said housing and generally along a vertical axis of said housing.

15. An air sterilization device as recited in claim 7 wherein said top of said housing has a generally dome shaped configuration and further wherein both said bottom and said top include a plurality of apertures formed therein.

16. An room air sterilization device as recited in claim 7 wherein each of said elongate members are formed by an extrusion process capable of defining said narrow, substantially parallel passages.

17. An air sterilization device as recited in claim 7 wherein each of said elongate members is at least five inches in length.

18. An air sterilization device as recited in claim 7 wherein a maximum distance of said ceramic material forming said elongate member between any two, adjacently disposed, narrow substantially parallel passages is less than a diameter of one of said narrow substantially parallel passages.

19. An air sterilization device as recited in claim 7 wherein a maximum distance of said ceramic material forming said elongate member between any two, adjacently disposed, narrow substantially parallel passages is generally about two millimeters.

20. An air sterilization device as recited in claim 7 wherein a thickness of said ceramic material between any two, adjacently disposed, narrow substantially parallel passages is generally about one and one-half (1.5) millimeters.

21. An air sterilization device as recited in claim 20 wherein a thickness of said ceramic material between an outer exposed wall defining said elongate member and any one of said narrow substantially parallel passages adjacent said outer exposed wall is at least generally about one and one-half (1.5) millimeters.

22. An air sterilization device as recited in claim 21 wherein said ceramic heating bundle comprises seven of said elongate members, each of said elongate members having seven of said narrow substantially parallel passages therein.

23. An air sterilization device as recited in claim 7 wherein said ceramic heating bundle comprises seven elongate members.

24. An air sterilization device as recited in claim 7 wherein an air sterilization capacity of said device can be increased by adding one or more of said elongate members to said bundle disposed within said housing.

25. An air sterilization device as recited in claim 7 wherein at least one of said heating wires is disposed in each of said narrow substantially parallel passages of each of said elongate member.

26. An air sterilization device as recited in claim 7 wherein said heating wire is formed of a nickel chromium material.

27. An air sterilization device as recited in claim 7 wherein said means for heating said heating wire include a power source structured and disposed to supply an electrical current to said heating wire and to cause a rise in temperature therein.

28. An air sterilization device as recited in claim 27 further comprising signal means for signaling when said air sterilization means are activated.

29. An air sterilization device as recited in claim 28 wherein said signal means include an exteriorly disposed light source structured to be illuminated when said air sterilization means are activated.

30. An air sterilization device as recited in claim 7 wherein said air sterilization means includes at least two of said heating wires, each of said heating wires being structured and disposed to be independently activated and to thereby, permit a user to selectively adjust a level of air sterilization.

31. An air sterilization device as recited in claim 7 further comprising an insulative material shell disposed in surrounding relation about said ceramic heating bundle and structured to minimize exterior heat loss therefrom.

32. An air sterilization device as recited in claim 7 further comprising a diffuser panel disposed above said ceramic heating bundle and structured to diffuse and thereby cool the air flowing out of said ceramic heating bundle.

* * * * *